(12) United States Patent
Azar

(10) Patent No.: US 8,939,962 B2
(45) Date of Patent: Jan. 27, 2015

(54) SYSTEM AND METHOD FOR URINARY CATHETERIZATION

(71) Applicant: Ramyar Azar, Tehran (IR)

(72) Inventor: Ramyar Azar, Tehran (IR)

( * ) Notice: Subject to any disclaimer, the term of this patent is extended or adjusted under 35 U.S.C. 154(b) by 0 days.

(21) Appl. No.: 14/101,634

(22) Filed: Dec. 10, 2013

(65) Prior Publication Data

US 2014/0100553 A1 Apr. 10, 2014

Related U.S. Application Data

(60) Provisional application No. 61/812,790, filed on Apr. 17, 2013.

(51) Int. Cl.
| | |
|---|---|
| *A61M 25/10* | (2013.01) |
| *A61M 25/12* | (2006.01) |
| *A61M 39/00* | (2006.01) |
| *A61M 39/10* | (2006.01) |
| *A61M 25/00* | (2006.01) |

(52) U.S. Cl.
CPC . *A61M 25/10184* (2013.01); *A61M 2210/1089* (2013.01); *A61M 25/1025* (2013.01); *A61M 25/1018* (2013.01); *A61M 2025/1068* (2013.01); *A61M 2025/1054* (2013.01); *A61M 25/0075* (2013.01); *A61M 25/10185* (2013.01); *A61M 2210/1085* (2013.01); *A61M 25/0017* (2013.01); *A61M 2210/1096* (2013.01)
USPC ..... 604/544; 604/540; 604/93.01; 604/96.01; 604/99.01; 604/99.02

(58) Field of Classification Search
CPC ............. A61M 2025/0175; A61M 2025/0188; A61M 2202/0496; A61M 2025/1061; A61M 2025/1065; A61M 25/00; A61M 25/0017; A61M 25/0068; A61M 25/0069; A61M 25/007; A61M 25/0071; A61M 25/0074; A61M 25/0075; A61M 25/10; A61M 25/1018; A61M 25/10184; A61M 25/10185; A61M 25/1025; A61M 2025/00; A61M 2025/0074; A61M 2025/0075; A61M 2025/0079; A61M 2025/1093; A61M 2025/1054; A61M 2025/1043
USPC ................ 604/540, 544, 93.01, 95.01, 95.02, 604/95.03, 96.01, 97.01, 99.01, 99.02, 604/99.04, 102.02, 102.03, 103, 103.03
See application file for complete search history.

(56) References Cited

U.S. PATENT DOCUMENTS

| | | | | | |
|---|---|---|---|---|---|
| 3,742,960 | A | * | 7/1973 | Dye et al. ................... | 604/99.03 |
| 3,837,347 | A | * | 9/1974 | Tower ........................... | 607/128 |
| 3,982,546 | A | * | 9/1976 | Friend ........................... | 604/249 |
| 4,210,478 | A | * | 7/1980 | Shoney ......................... | 156/242 |
| 4,517,979 | A | * | 5/1985 | Pecenka ........................ | 606/195 |
| 5,100,385 | A | * | 3/1992 | Bromander ................. | 604/99.03 |
| 5,217,434 | A | * | 6/1993 | Arney ........................ | 604/99.04 |

(Continued)

*Primary Examiner* — Adam Marcetich
(74) *Attorney, Agent, or Firm* — Barry Choobin; Patent 360 LLC

(57) ABSTRACT

The embodiments herein provide an atraumatic urinary catheter. The atraumatic urinary catheter has a first tubule, a second tubule and a third tubule. The first tubule is provided with a first channel and a second channel. The first channel is wide and extended from a proximal end to a distal end of the first tubule and the first channel is open in both ends. The second tubule comprises a third channel, which is connected to a bladder cavity. The third tubule placed on the first tubule and the second tubule as a cover, to form a catheter's balloon. In order to avoid balloon explosion, the sterile water in the balloon is drained by the self-retaining mechanism of the catheter to prevent an irritation and tissue traumatization.

5 Claims, 7 Drawing Sheets

(56) References Cited

U.S. PATENT DOCUMENTS

| | | | |
|---|---|---|---|
| 5,378,238 A * | 1/1995 | Peters et al. | 604/99.04 |
| 6,506,179 B1 * | 1/2003 | Tiefenthal et al. | 604/103.06 |
| 2002/0198558 A1 * | 12/2002 | Briscoe et al. | 606/192 |
| 2004/0220522 A1 * | 11/2004 | Briscoe et al. | 604/99.04 |
| 2004/0236366 A1 * | 11/2004 | Kennedy et al. | 606/192 |
| 2011/0094655 A1 * | 4/2011 | Wiita et al. | 156/157 |
| 2011/0098683 A1 * | 4/2011 | Wiita et al. | 604/544 |
| 2013/0103005 A1 * | 4/2013 | Kalser et al. | 604/544 |
| 2013/0237965 A1 * | 9/2013 | Pinchuk et al. | 604/544 |

* cited by examiner

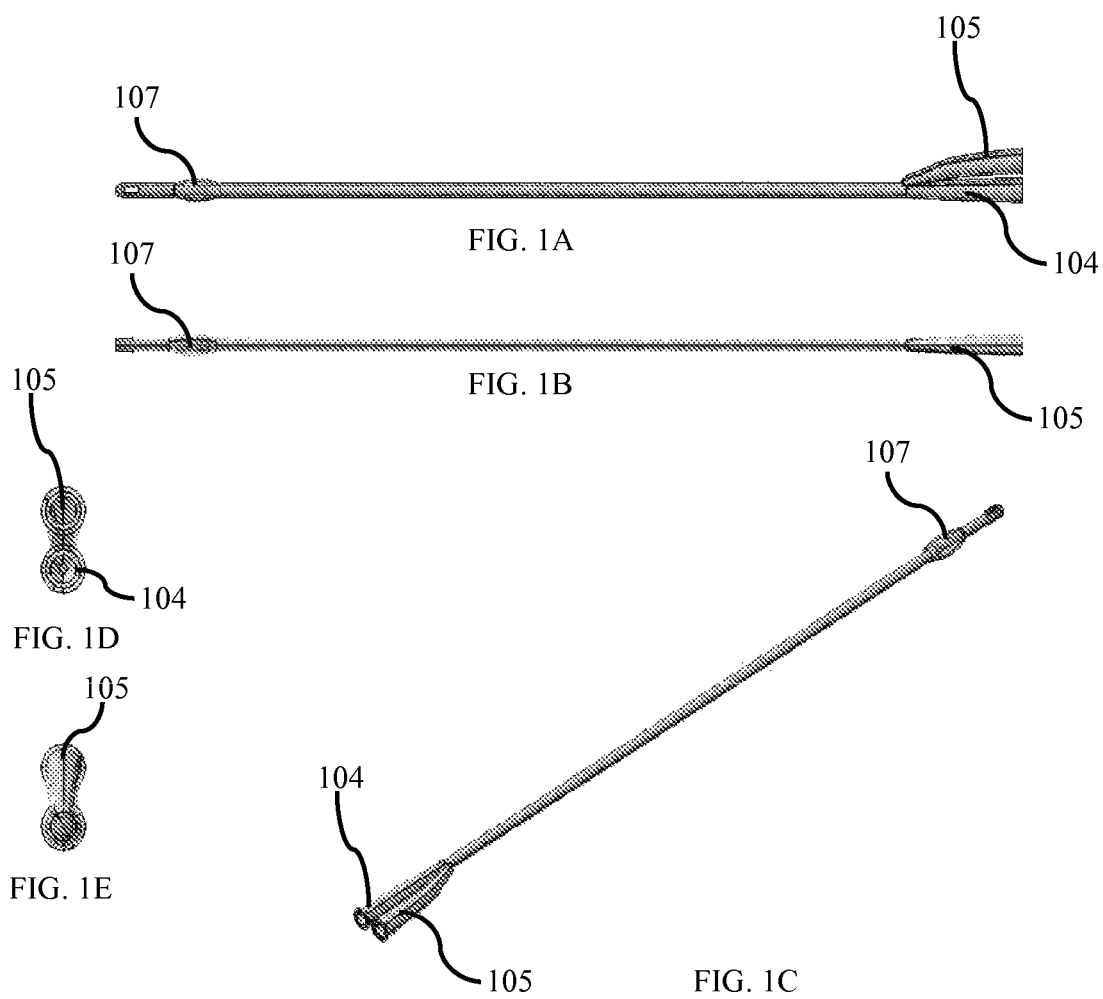

SYSTEM AND METHOD FOR URINARY CATHETERIZATION

CROSS REFERENCE TO RELATED APPLICATION

The present invention claims priority of a provisional application filed on Apr. 17, 2013, with Ser. No. 61/812,790.

BACKGROUND

1. Technical Field

The embodiments herein generally relate to urinary bladder catheters and particularly relates to a drainage mechanism for urinary catheters. The embodiments herein particularly relates to an indwelling, atraumatic urinary catheter with a safe retaining mechanism for draining the bladders during any medical procedures and in acute and chronic medical or surgical conditions rapidly to prevent an explosion and tissue traumatization.

2. Description of the Related Art

In many health care services, the urinary catheters are found useful in draining the bladders. The currently available catheters are often flexible tubes that are passed through the urethra into the bladder and provided with a fluid-refillable balloon element at the distal end. The main purpose of the balloon is to keep the catheter in the bladder securely. Furthermore, the full balloon, which is placed, on the bladder outlet prevents any leakage of the urine into the urethra so that the catheter will be the only way for draining the urine.

A common type of urinary catheters, also known as Foley catheters, has a balloon at the distal end. After the Foley catheter is inserted into the urethra and the bladder is reached, the balloon is filled with sterile water so that the inflated balloon prevents the catheter from escaping out. The Foley catheter is one of the most practical instruments in the medicine and is available in different sizes and different materials depending on the patient's age and medical problem. Some of the usages of the Foley are as follows.

The patients who are anesthetized or sedated for surgery or other medical care are catheterized since they are unable to control their urine. Measuring the hourly urinary output is an important parameter for monitoring patients after surgeries or calculating their response to some medications such as diuretics.

A patient, whose prostate is enlarged to the point that urine flow is cut-off, has to be catheterized and the catheter has to be kept in until the problem is resolved. In a prostate surgery, a post-operative bleeding is common, and when it left unchecked, the blood clots are formed in the bladder, which obstructs catheters tubule. In order to prevent the obstruction, three-way catheters are usually used to allow the bladder to be washed.

In chronic medical or surgical conditions, the urinary bladder has to be drained for weeks, months or in some cases for years. Examples of such conditions include comatose patients, diffuse axonal injury patients, the patients in vegetative stage for their rest of their life, etc.

Although the urinary Foley catheter is a very useful device in medicine, they have several disadvantages, which adversely affect on the health of a patient. One of the main problems occurs is a urethra injury or a tearing of a urethra when there is an accidental inflation of the catheters balloon inside the urethra instead of the bladder. The inflation causes urethra injury and even urethra tear. A partial or complete tear of the bladder leaves a scar, which narrows the urethra and also has a great chance for developing an infection.

Further, damage occurs during the removal of the catheter, when the balloon is not completely deflated. This causes a urethra injury or tear due to the fact that old patients or traumatized urethras are unable to expand enough thereby developing a tear in the urethral wall. A tear in urethral wall is also possible due to an accidental pulling off of the catheter while the balloon is still inflated inside the body. This is very frequent due to unconsciousness of the patients, patient's age and oftentimes in the emergency rooms. The pulling off catheter during the inflated condition of the balloon, is very painful and traumatizing the urethra which lead to serious health problems. In the case of a long-term use of the catheter, the balloon fails to deflate when the catheter is to be removed. This situation requires some complicated invasive procedures in order to puncture the balloon inside the urinary bladder.

Hence there is a need for an improved catheter system that eliminates safety issues and aforementioned problems with a balloon retention system faced by the current catheters. There is also need for a durable system that fulfills the need for long lasting usage.

The above-mentioned shortcomings, disadvantages and problems are addressed herein and which will be understood by reading and studying the following specification.

OBJECTS OF THE EMBODIMENTS

The primary object of the embodiments herein is to provide a safe indwelling catheter system with an improved retaining mechanism for the patients.

Another object of the embodiments herein is to provide an indwelling catheter for emptying the bladder in acute and chronic medical or surgical conditions.

Yet another object of the embodiments herein is to provide an indwelling catheter for draining a bladder freely during any medical procedures.

Yet another object of the embodiments herein is to provide an indwelling catheter with a self-retaining mechanism arranged in the catheter's balloons cavity and located in the shaft of the catheter for allowing the catheter to be removed from the bladder with no tissue traumatization.

Yet another object of the embodiments herein is to provide an indwelling catheter with a self-retaining mechanism to allow the balloon to deflate rapidly, to prevent a balloon explosion and tissue traumatization, when a pressure inside a balloon is increased suddenly to a point of balloon explosion.

These and other objects and advantages of the present disclosure will become readily apparent from the following detailed description taken in conjunction with the accompanying drawings.

SUMMARY

The various embodiments provide an atraumatic urinary catheter. The atraumatic urinary catheter comprises a first tubule, a second tubule and a third tubule. The first tubule comprises a first channel and a second channel. The first channel is wide and extended from a proximal end of the first tubule to a distal end of the first tubule and the first channel is open at both the proximal end and distal end. The second tubule comprises a third channel and the third channel of the second tubule is connected to a bladder cavity. The third tubule placed on the first tubule and the second tubule as a cover, and the third tubule produces a catheter's balloon.

According to an embodiment herein, a self-retaining mechanism is produced in the third tubule at the junction of the first tubule and the second tubule in the catheter's balloons cavity.

According to an embodiment herein, the second channel of the first tubule is thin and the second channel is connected to the catheter's balloon. The catheter's balloon is filled with sterile water through the second channel.

According to an embodiment herein, the self-retaining mechanism is produced by placing a thin distal end of the first channel of the first tubule inside a wide proximal end of the third channel of the second tubule and covering the first tubule and the second tubule with the third tubule.

According to an embodiment herein, the thin distal end of the first channel of the first tubule of the self-retaining mechanism is detached from the wide proximal end of the third channel of the second tubule to deflate catheter's balloon, when a pressure of catheter's balloon is increased to a pre-set point.

According to an embodiment herein, the first channel of the first tubule and the third channel of the second tubule are connected together to produce a main longitudinal channel within the catheter. The main longitudinal channel is extended from the proximal end of the first tubule to a first hole. The urine is drained from a bladder through the first hole.

According to an embodiment herein, the third tubule is connected to the first tubule and the second tubule firmly except at the junction of the first tubule and the second tubule. The catheter's balloon is produced by the part of the third tubule at the junction of the first tubule and the second tubule.

According to an embodiment herein, the second channel of the first tubule is a filling channel adopted inside a wall of the first tubule. The second channel is extended from the proximal end of the first tubule to a second hole. The second hole is connected to the balloons cavity for filling sterile water.

According to an embodiment herein, the balloon's pressure rises suddenly when the catheter is pulled off and the balloon is inflated in the bladder. The balloon's pressure forces the distal end of the first tubule to detach from the second tubule allowing the sterile water inside the balloons cavity to be drained by the first channel of the first tubule and the third channel of the second tubule allowing the catheter to be removed from the bladder with no tissue traumatization.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which:

FIG. 1A illustrates a front side view of an atraumatic urinary catheter, according to one embodiment herein.

FIG. 1B illustrates a top side view of an atraumatic urinary catheter, according to one embodiment herein.

FIG. 1C illustrates a top side perspective view of an atraumatic urinary catheter, according to one embodiment herein.

FIG. 1D illustrates a right side view of an atraumatic urinary catheter, according to one embodiment herein.

FIG. 1E illustrates a left side view of an atraumatic urinary catheter, according to one embodiment herein.

DETAILED DESCRIPTION OF THE EMBODIMENTS

Figure 2A:
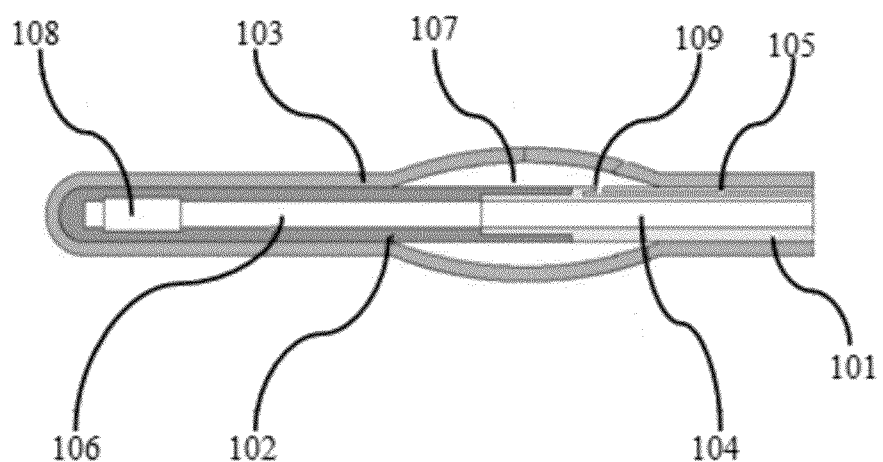
FIG. 2A illustrates an enlarged cross sectional view of one end an atraumatic urinary catheter indicating a balloon cavity according to one embodiment herein.

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments provide an atraumatic urinary catheter. The atraumatic urinary catheter comprises a first tubule, a second tubule and a third tubule. The first tubule comprises a first channel and a second channel. The first channel is wide and extended from a proximal end of the first tubule to a distal end of the first tubule and the first channel is open at both the proximal end and distal end. The second tubule comprises a third channel and the third channel of the second tubule is connected to a bladder cavity. The third tubule placed on the first tubule and the second tubule as a cover, and the third tubule produces a catheter's balloon.

According to an embodiment herein, a self-retaining mechanism is produced in the third tubule at the junction of the first tubule and the second tubule in the catheter's balloons cavity.

According to an embodiment herein, the second channel of the first tubule is thin and the second channel is connected to the catheter's balloon. The catheter's balloon is filled with sterile water through the second channel.

According to an embodiment herein, the self-retaining mechanism is produced by placing a thin distal end of the first channel of the first tubule inside a wide proximal end of the third channel of the second tubule and covering the first tubule and the second tubule with the third tubule.

According to an embodiment herein, the thin distal end of the first channel of the first tubule of the self-retaining mechanism is detached from the wide proximal end of the third channel of the second tubule to deflate catheter's balloon, when a pressure of catheter's balloon is increased to a pre-set point.

According to an embodiment herein, the first channel of the first tubule and the third channel of the second tubule are connected together to produce a main longitudinal channel within the catheter. The main longitudinal channel is extended from the proximal end of the first tubule to a first hole. The urine is drained from a bladder through the first hole.

According to an embodiment herein, the third tubule is connected to the first tubule and the second tubule firmly except at the junction of the first tubule and the second tubule. The catheter's balloon is produced by the part of the third tubule at the junction of the first tubule and the second tubule.

According to an embodiment herein, the second channel of the first tubule is a filling channel adopted inside a wall of the first tubule. The second channel is extended from the proximal end of the first tubule to a second hole. The second hole is connected to the balloons cavity for filling sterile water.

According to an embodiment herein, the balloon's pressure rises suddenly when the catheter is pulled off and the balloon is inflated in the bladder. The balloon's pressure forces the distal end of the first tubule to detach from the second tubule allowing the sterile water inside the balloons cavity to be drained by the first channel of the first tubule and the third channel of the second tubule allowing the catheter to be removed from the bladder with no tissue traumatization.

FIG. 1A-1B illustrates a schematic representation of an atraumatic urinary catheter, according to one embodiment herein. FIG. 1A illustrates a front view of the catheter. FIG. 1B illustrates a top view of the catheter. FIG. 1C illustrates an isometric view of the catheter. FIG. 1D illustrates a right side view of the catheter and FIG. 1E illustrates a left side view of the catheter. With respect to FIG. 1A-1B, the atraumatic urinary catheter comprises a first tubule comprising a first channel 104 and a second channel 105. The first channel 104 is wide and extended from a proximal end of the first tubule to a distal and the first channel 104 is open at both the ends. The second channel 105 of the first tubule is thin and is connected to the catheter's balloon 107 as shown in FIGS. 1A, 1B and 1C. The catheter's balloon 107 is filled with sterile water through the second channel 105.

Figure 2B:
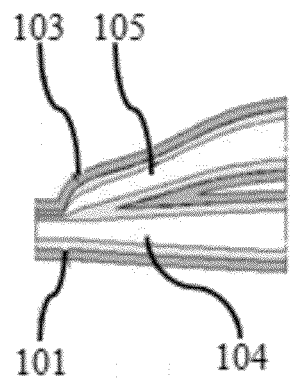
FIG. 2B illustrates an enlarged cross sectional view of other end of an atraumatic urinary catheter provided with a self retaining mechanism, according to one embodiment herein.

FIG. 2A-2B illustrates a cross sectional view of an atraumatic urinary catheter, according to one embodiment herein. FIG. 2A illustrates an enlarged cross sectional view of one end an atraumatic urinary catheter indicating a balloon cavity, while FIG. 2B illustrates an enlarged cross sectional view of other end of an atraumatic urinary catheter provided with a self retaining mechanism, according to one embodiment herein. With respect to FIG. 2A-2B, the atraumatic urinary catheter comprises a first tubule 101 comprising a first channel 104 and a second channel 105. The first channel 104 is wide and extended from a proximal end of the first tubule 101 to a distal and the first channel 104 is open on both the ends. The second channel 105 of the first tubule 101 is thin and is connected to the catheter's balloon 107 as shown in FIGS. 2A and 2B. The catheter's balloon 107 is filled with sterile water through the second channel 105 through a hole 109.

The second tubule 102 is distal and has one channel 106, which is connected, to the bladder cavity by the hole 108. The first tubule 101 is thin at its distal end and whereas the third channel 106 is wide at the proximal end. The second tubule 102 is placed along the longitudinal axis of the first tubule 101 while the distal end of the first tubule 101 is placed inside the proximal end of the second channel 106 which allows the first channel 104 to connect the second channel 106 together to form the main longitudinal channel of the catheter which is extended from the proximal end of the first tubule 101 to the hole 108. The third tubule 103 is placed on the first tubule 101 and the second tubule 102 and covers both the first tubule 101 and the second tubule 102. The third tubule 103 is connected to the first tubule 101 and the second tubule 102 firmly/tightly except in the junction part of the first tubule 101 and the second tubule 102.

The balloon 107 is formed by the part of the third tubule 103, which is not connected to the junction of the first tubule 101, and the second tubule 102.

The self-retaining mechanism is produced by the junction of first tubule 101 and the second tubule 102 in the balloons cavity 107 where the distal end of the first tubule 101 is placed inside the proximal end of second channel 106 (as shown in FIGS. 2B-2C).

Figure 3A:
FIG. 3A illustrates a cross sectional view of one end of an atraumatic urinary catheter shown in FIG. 2A, according to one embodiment herein.
Figure 3B:
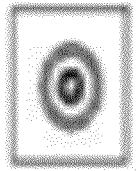
FIG. 3B illustrates a cross sectional view of a balloon area in an atraumatic urinary catheter, according to one embodiment herein.
Figure 3C:
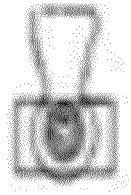
FIG. 3C illustrates a cross sectional view of another end of an atraumatic urinary catheter shown in FIG. 2B, according to one embodiment herein.
Figure 3D:
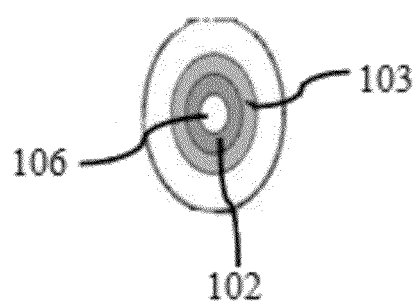
FIG. 3D illustrates an enlarged cross sectional view of one end of an atraumatic urinary catheter shown in FIG. 3A, according to one embodiment herein.
Figure 3E:
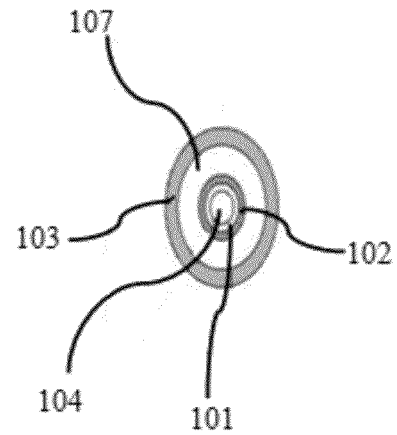
FIG. 3E illustrates an enlarged cross sectional view of a balloon area of an atraumatic urinary catheter shown in FIG. 3B, according to one embodiment herein.
Figure 3F:
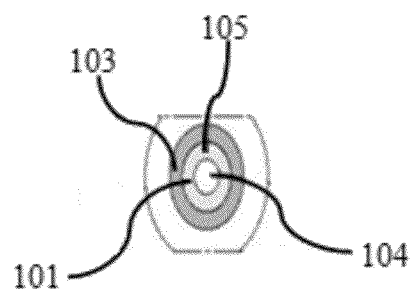
FIG. 3F illustrates an enlarged cross sectional view of another end of an atraumatic urinary catheter shown in FIG. 3C, according to one embodiment herein.

FIG. 3A-3F illustrates a cross section of an atraumatic urinary catheter, according to one embodiment herein. FIG. 3A illustrates a cross sectional view of one end of an atraumatic urinary catheter shown in FIG. 2A, according to one embodiment herein. FIG. 3B illustrates a cross sectional view of a balloon area in an atraumatic urinary catheter, according to one embodiment herein. FIG. 3C illustrates a cross sectional view of another end of an atraumatic urinary catheter shown in FIG. 2B, according to one embodiment herein. FIG. 3D illustrates an enlarged cross sectional view of one end of an atraumatic urinary catheter shown in FIG. 3A, according to one embodiment herein. FIG. 3E illustrates an enlarged cross sectional view of a balloon area of an atraumatic urinary catheter shown in FIG. 3B, according to one embodiment herein. FIG. 3F illustrates an enlarged cross sectional view of another end of an atraumatic urinary catheter shown in FIG. 3C, according to one embodiment herein.

With respect to FIG. 3A-3F, the third tubule 103 is placed on the first tubule 101 and the second tubule 102 and covers them. The third tubule 103 is connected to the first tubule 101 and the second tubule 102 firmly except in the junction part.

The balloon 107 is formed by the part of the third tubule 103, which is not connected to the junction of the first tubule 101 and the second tubule 102. The second tubule 102 is placed along the longitudinal axis of the first tubule 101, while the distal end of the first tubule 101 is inside the proximal end of the channel 106 which allows the first channel 104 to connect the second channel 106 and together make the main longitudinal channel of the catheter which is extended from the proximal end of the first tubule 101 to the hole. The second channel 105 of the first tubule 101 is thin and is connected to the catheter's balloon 107.

Figure 4A:
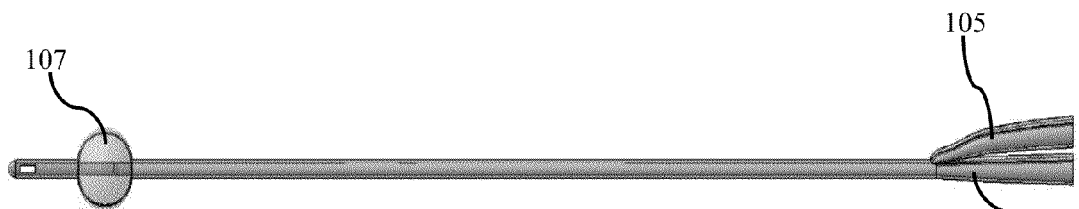
FIG. 4A illustrates a front side view an atraumatic urinary catheter with the balloon in inflated condition, according to one embodiment herein.
Figure 4B:
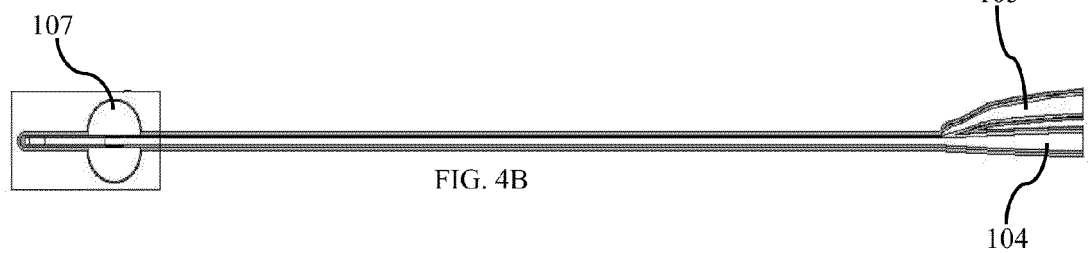
FIG. 4B illustrates a side sectional view of an atraumatic urinary catheter with the balloon in inflated condition, according to one embodiment herein.
Figure 4C:
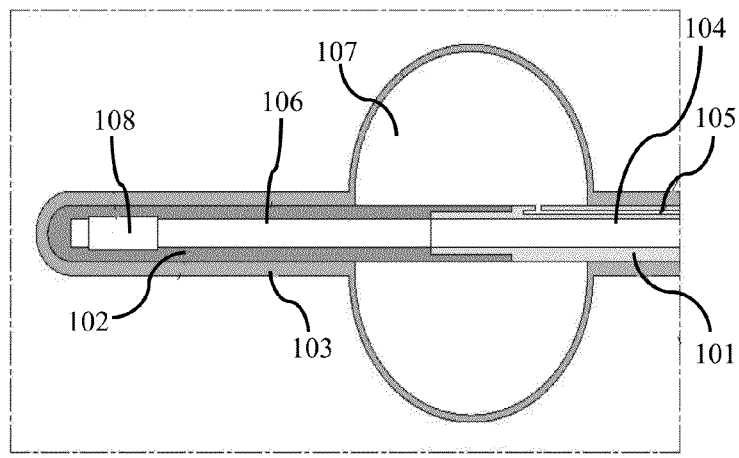
FIG. 4C illustrates an enlarged cross sectional view of a self retaining mechanism in an atraumatic urinary catheter with the balloon in inflated condition, according to one embodiment herein.

FIG. 4A-4C illustrates a schematic representation of an atraumatic urinary catheter when the balloon is inflated, according to one embodiment herein. FIG. 4A illustrates a front side view an atraumatic urinary catheter with the balloon in inflated condition, according to one embodiment herein. FIG. 4B illustrates a side sectional view of an atraumatic urinary catheter with the balloon in inflated condition, according to one embodiment herein. FIG. 4C illustrates an enlarged cross sectional view of a self retaining mechanism in an atraumatic urinary catheter with the balloon in inflated condition, according to one embodiment herein.

With respect to FIG. 4A-4C, the second channel 105 is a filling channel in the wall of the first tubule 101 and is extended from the proximal end of the first tubule 101 to the hole, which connects first tubule 101 to the balloon cavity 107. The second channel 105 has a role of filling the balloon 107 with the sterile water. The first channel 104 is connected to the third channel 106 and together form the main longitudinal channel of the catheter, which is extended, from the proximal end of the first tubule 101 to the hole 108. The third tubule 103 is placed on the first tubule 101 and the second tubule 102 and covers them. The third tubule 103 is connected to the first tubule 101 and the second tubule 102 firmly except in the junction part. The balloon 107 is formed by the part of the third tubule 103, which is not connected to the junction of the first tubule 101 and the second tubule 102.

Figure 5A:
FIG. 5A illustrates a front side view an atraumatic urinary catheter with the self retaining mechanism in activated condition and the balloon in deflated condition, according to one embodiment herein.
Figure 5B:
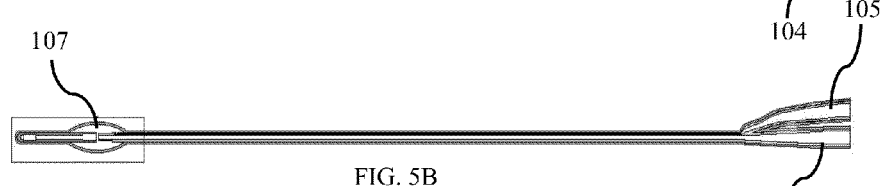
FIG. 5B illustrates a side sectional view of an atraumatic urinary catheter with the self-retaining mechanism in activated condition and the balloon in deflated condition, according to one embodiment herein.
Figure 5C:
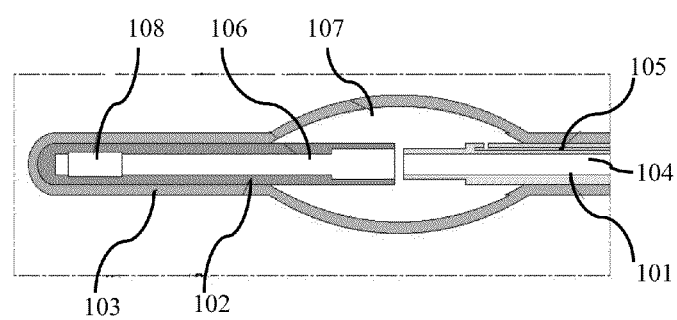
FIG. 5C illustrates an enlarged cross sectional view of a self retaining mechanism in activated condition and the balloon in deflated condition in an atraumatic urinary catheter, according to one embodiment herein.

FIG. 5A-5C illustrates a schematic representation of an atraumatic urinary catheter when the balloon is inflated, according to one embodiment herein. FIG. 5A illustrates a front side view an atraumatic urinary catheter with the self retaining mechanism in activated condition and the balloon in deflated condition, according to one embodiment herein. FIG. 5B illustrates a side sectional view of an atraumatic urinary catheter with the self-retaining mechanism in activated condition and the balloon in deflated condition, according to one embodiment herein. FIG. 5C illustrates an enlarged cross sectional view of a self retaining mechanism in activated condition and the balloon in deflated condition in an atraumatic urinary catheter, according to one embodiment herein.

With respect to FIG. 5A-5C, the first channel 104 is connected to the third channel 106 and together form the main longitudinal channel of the catheter, which is extended, from the proximal end of the first tubule 101 to the hole 108. The self-retaining mechanism is produced at the junction of the first tubule 101 and the second tubule 102 in the balloons cavity 107 of the third tubule 103 where the distal end of the first tubule 101 is placed inside the proximal end of the third channel 106. When the balloons cavity 107 is inflated in the bladder while catheter is being pulled off from the bladder, the balloon 107 pressure rises suddenly. This situation forces the distal end of the first tubule 101 out of the third channel 106, so that the sterile water in the balloons cavity 107 is drained by the channels 104 and 106, and the catheter is removed with no tissue traumatization. The second channel 105 of the first tubule 101 is thin and is connected to the catheter's balloon 107. The catheter's balloon 107 is filled with sterile water through the second channel 105 through a hole.

According to one embodiment herein, the point of pressure in which the self-retaining mechanism works depends on the length of the thin distal end of the first tubule 101 that is placed in the third channel 106 and the length of distal end various in different catheters depending on the patient's age, medical problem and catheters balloon capacity.

Figure 6:
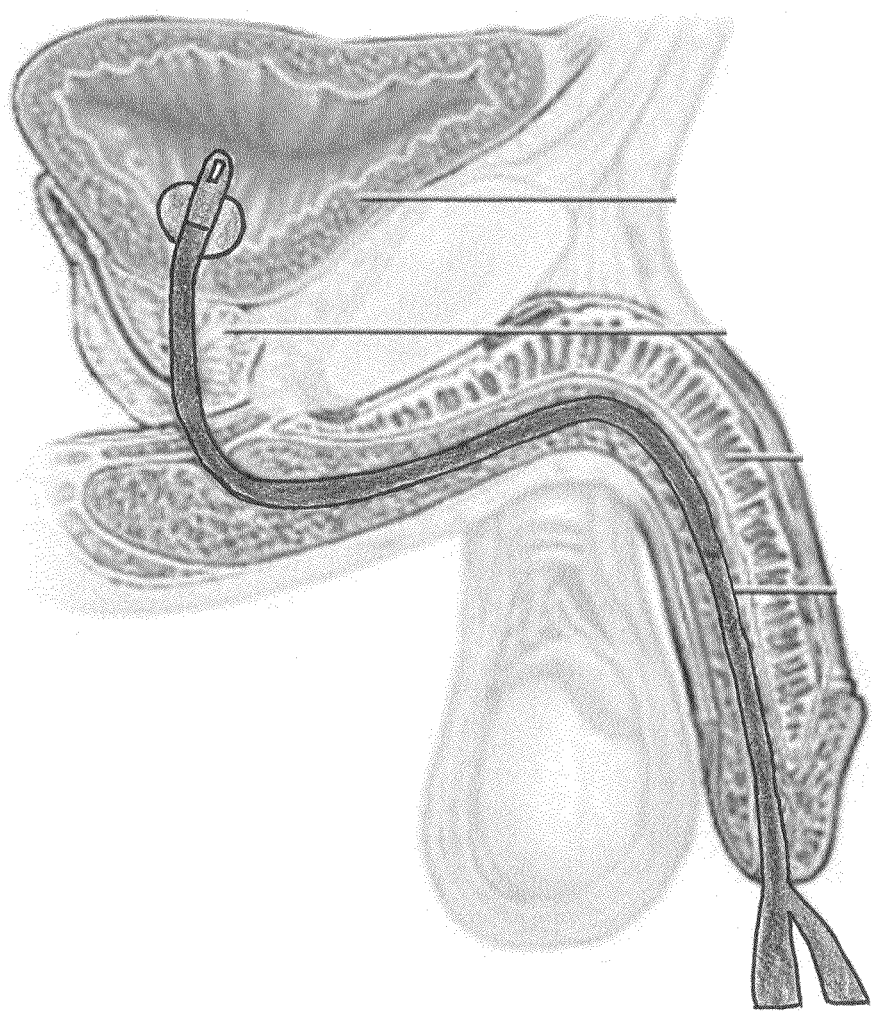
FIG. 6 illustrates a side view of an atraumatic urinary catheter, when the catheter is inserted in the body and the balloon is inflated, according to one embodiment herein.

FIG. 6 illustrates a side view of an atraumatic urinary catheter, when the catheter is inserted in the body and the balloon is inflated, according to one embodiment herein.

When the balloon is inflated in the bladder, during the removal of the catheter, the balloons pressure rises suddenly which forces the distal end of first tubule out of the third channel, so that the sterile water of the balloons cavity is drained by the first and third channels, and the catheter is removed with no tissue traumatization.

Figure 7:
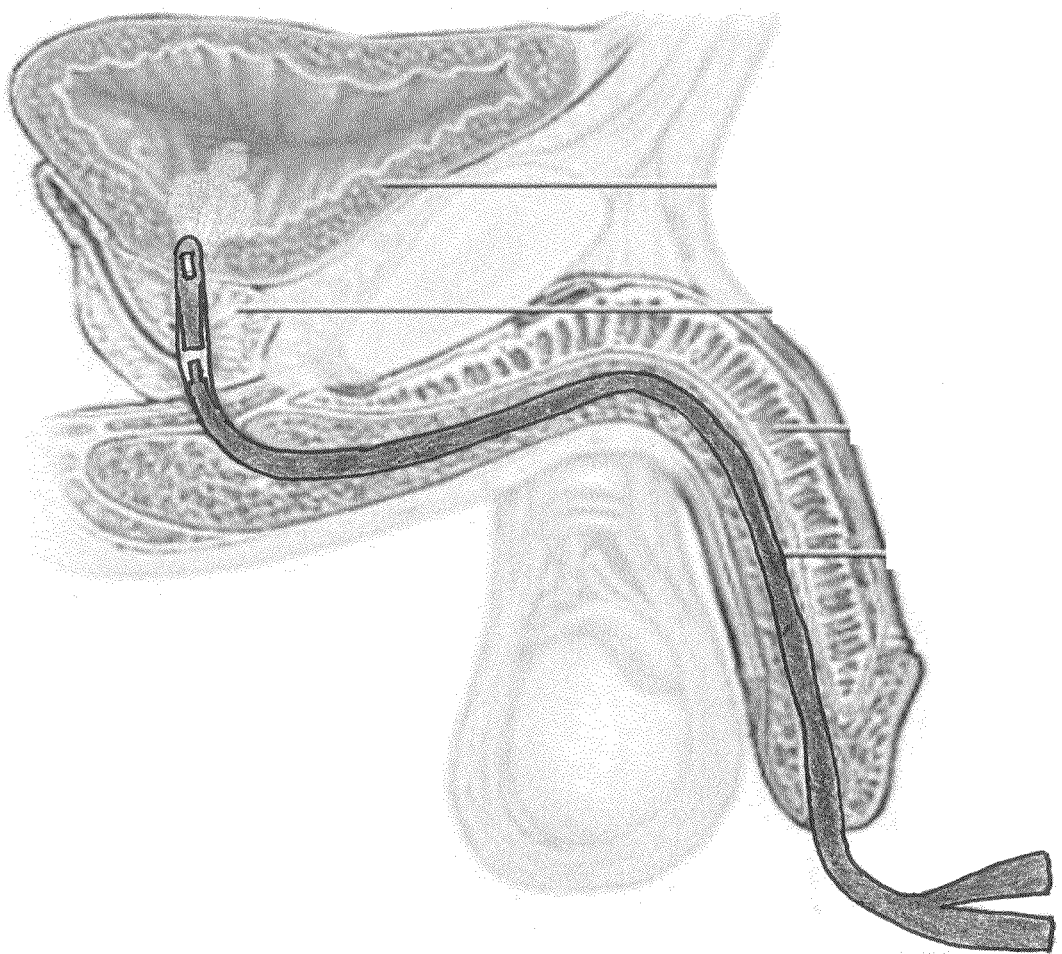
FIG. 7 illustrates a side view of an atraumatic urinary catheter during a removal of the catheter when the balloon in deflated by the self-retaining mechanism, according to one embodiment herein.

FIG. 7 illustrates a side view of an atraumatic urinary catheter during a removal of the catheter when the balloon in deflated by the self-retaining mechanism, according to one embodiment herein. The atraumatic urinary catheter of the present disclosure is safe to use by the patients. The atraumatic urinary catheter is durable and fulfills the need of long lasting usage.

The point of pressure in which the self-retaining mechanism works depends on the length of the thin distal end of the first tubule, which is placed in the third channel, and the pressure is different for different catheters depending on the patient's age, medical problem and catheters balloon capacity.

The urinary catheter of the embodiments herein has an improved retaining mechanism, which is located inside the shaft of the catheter in the balloons cavity. When the balloon's pressure rises suddenly to the point of balloon explosion, the retaining mechanism allows the balloon to deflate rapidly in order to prevent the explosion and tissue traumatization, by draining the sterile water in the balloon.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the disclosure with modifications. However, all such modifications are deemed to be within the scope of the claims.

It is also to be understood that the following claims are intended to cover all of the generic and specific features of the embodiments described herein and all the statements of the scope of the embodiments, which as a matter of language might be said to fall there between.

What is claimed is:

1. An atraumatic urinary catheter, the catheter comprising:
   a first tubule comprising a first channel and a second channel, and wherein the first channel is wide and extended from a proximal end of the first tubule to a distal end of the first tubule, and wherein the first channel is open in both ends;

a second tubule comprising a third channel, and wherein the third channel of the second tubule is configured to communicate with a bladder cavity; and a third tubule placed on the first tubule and the second tubule as a cover, and wherein the third tubule produces a catheter balloon;

wherein a self-retaining mechanism is formed in the third tubule at a junction of the first tubule and the second tubule in a catheter balloon cavity, and wherein the self-retaining mechanism is formed by placing a thin distal end of the first channel of the first tubule inside a wide proximal end of the third channel of the second tubule to cover both the first tubule and the second tubule within the third tubule, and wherein the thin distal end of the first channel of the first tubule of the self-retaining mechanism is detached from the wide proximal end of the third channel of the second tubule to deflate the catheter balloon when a pressure of the catheter balloon rises to a pre-set point, and wherein the first channel of the first tubule and the third channel of the second tubule are connected together to produce a main longitudinal channel within the catheter, and wherein the main longitudinal channel extends from the proximal end of the first tubule to a first hole, and wherein urine is drained from bladder through the first hole, and wherein the self retaining mechanism opens or activates only, when the thin distal end of the first channel of the first tubule of the self-retaining mechanism is completely separated or detached from the wide proximal end of the third channel of the second tubule to deflate the catheter balloon.

2. The catheter according to claim 1, wherein the second channel of the first tubule is thin, and wherein the second channel is connected to the catheter balloon, and wherein the catheter balloon is filled with sterile water through the second channel.

3. The catheter according to claim 1, wherein the third tubule is connected to the first tubule and the second tubule except at a junction of the first tubule and the second tubule, and wherein the catheter balloon is produced by a part of the third tubule at the junction of the first tubule and the second tubule.

4. The catheter according to claim 1, wherein the second channel of the first tubule is a filling channel adopted in an inner side wall of the first tubule, and wherein the second channel is extended from the proximal end of the first tubule to a second hole, and wherein the second hole is connected to the balloon cavity for filling sterile water.

5. The catheter according to claim 1, wherein the pressure of balloon cavity rises suddenly when the catheter is pulled off and the balloon is inflated in the bladder, and wherein the pressure of balloon cavity forces the distal end of the first tubule to detach from the second tubule allowing the sterile water inside the balloon cavity to be drained by the first channel of the first tubule and the third channel of the second tubule.

* * * * *